United States Patent
Tsai et al.

(10) Patent No.: US 6,420,304 B1
(45) Date of Patent: Jul. 16, 2002

(54) POLYMER-SUPPORTED CARBONYLATION CATALYST AND ITS USE

(75) Inventors: Chia-Jung Tsai; Yao-Lung Liu, both of Kaohsiung; Hsi-Chin Tsai, Chiya-Yi, all of (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 09/553,054

(22) Filed: Apr. 20, 2000

(51) Int. Cl.[7] .......................... B01J 21/02; C07C 51/14; C07C 51/56
(52) U.S. Cl. ..................... 502/207; 502/105; 502/151; 502/152; 502/159; 502/200; 502/313; 562/518; 562/517; 562/497; 562/606; 562/607; 562/890; 562/891; 562/519
(58) Field of Search ................................. 502/105, 151, 502/152, 200, 159, 207, 513; 562/519, 518, 517, 497, 606, 607, 890, 891

(56) References Cited

U.S. PATENT DOCUMENTS

| | | | |
|---|---|---|---|
| 3,652,678 A | * | 3/1972 | Allum et al. |
| 3,769,329 A | * | 10/1973 | Paulik et al. |
| 3,987,009 A | * | 10/1976 | Young |
| 3,998,887 A | * | 12/1976 | Allen |
| 4,100,359 A | * | 7/1978 | Schmerling et al. |
| 4,325,834 A | * | 4/1982 | Bartish et al. |
| 4,690,912 A | * | 9/1987 | Paulik et al. |
| 4,733,006 A | * | 3/1988 | Singelton et al. |
| 5,001,259 A | * | 3/1991 | Smith et al. |
| 5,364,963 A | * | 11/1994 | Minami et al. ............. 502/326 |
| 5,442,107 A | * | 8/1995 | Beevor et al. |
| 5,455,874 A | * | 10/1995 | Ormsby et al. ............. 358/433 |
| 5,466,874 A | * | 11/1995 | Scates et al. |
| 6,066,762 A | * | 5/2000 | Yoneda et al. ............. 562/517 |

FOREIGN PATENT DOCUMENTS

EP 0277824 * 10/1988

* cited by examiner

Primary Examiner—Paul J. Killos
Assistant Examiner—Robert W. Deemie
(74) Attorney, Agent, or Firm—Bacon & Thomas

(57) ABSTRACT

The invention relates to a polymer-supported carbonylation catalyst and its use in a process for preparing organic carboxylic acid or anhydride having n+1 carbon atoms. The invention relates also to a process for preparing organic carboxylic acid or anhydride having n+1 carbon atoms by carbonylating with monoxide, in the presence of the above-mentioned carbonylation catalyst, on alcohols having n carbon atoms, ethers having 2n carbon atoms or esters formed from said alcohols and acids. In particular, the invention relates to a process for preparing acetic acid by carbonylating methanol with carbon monooxide in the presence of said carbonylation catalyst. By using said carbonylation catalyst, the temperature for carbonylation can be lowered to about 160° C. with a reaction rate better than that of a traditional process, while the tendency of catalyst precipitation in the course of carbonylation can be improved also. The process can be operated normally as the concentration of rhodium increased to up to several thousand ppm. Further, a comparable reaction rate can be achieved in the absence of water and hydroiodic acid, whereby the corrosion problem of the equipment and promotion of production capacity can be improved significantly.

36 Claims, No Drawings

POLYMER-SUPPORTED CARBONYLATION CATALYST AND ITS USE

BACKGROUND OF THE INVENTION

The invention relates to a polymer-supported carbonylation catalyst and its use in a process for preparing organic carboxylic acids or anhydrides having n +1 carbon atoms.

The invention relates also to a process for preparing organic carboxylic acids or anhydrides having n +1 carbon atoms by reacting, in the presence of the above-mentioned carbonylation catalyst, an alcohol having n carbon atoms, an ether having 2n carbon atoms or an ester formed from said alcohol and acid with carbon monoxide. In particular, the invention relates to a process for preparing acetic acid by reacting methanol with carbon monoxide in the presence of said carbonylation catalyst.

The most commonly known process for preparing acetic acid up to date has been the process described by Paulik et al. in U.S. Pat. Nos. 3,769,329 and 4,690,912. That process comprised synthesizing acetic acid through a carbonylation reaction of carbon monoxide and methanol in the presence of a rhodium catalyst at a temperature of 180° C., and a carbon monoxide pressure of 35–70kg/cm$^2$ as well as using methyl iodide as promoter. These patents disclosed that the most effective solvent for the production reaction of acetic acid was the product, acetic acid, itself. Its main advantages were that the catalyst had very high conversion and selectivity (>95%), had a relatively long service life, and could be recycled almost completely to the reactor. However, water content in those reaction system should be maintained at least higher than 14–15wt. % in order to prevent the rhodium catalyst from precipitation and keep a relatively high reaction rate. Such high water content would increase the cost of equipment used in the purification process and consume considerable energy that it becomes so-called a "high water content" carbonylation process.

Thereafter, there have been a number of patents proposing improved methods with respect to this acetic acid process. The main objective of those patents was aimed at increasing the stability of the rhodium catalyst under low water content (<14 wt. %) in order to alleviate the corrosion problem of moisture reaction to the equipment and also reduce largely the energy consumption during isolation and purification of the product. Namely, they were developed toward a "low water content" carbonylation process. Their main approaches comprised of (1) incorporating inorganic or organic salts as additives in the reaction medium, (2) using supported catalyst by combing the rhodium catalyst with a polymer, active carbon or ion exchange resin, and (3) using both of (1) and (2).

U.S. Pat. No. 4,733,006 disclosed the use of an inorganic salt XOAc (X=Li$^+$,Na$^+$,K$^+$) as additives. However, it did not teach the effect of these inorganic salts on the reaction rate throughout the entire disclosure. EP 55618 disclosed a technique to reduce the precipitation of the rhodium catalyst due to low water content during the carbonylation of methanol by adding an organic catalyst stabilizer in the reaction solution. Stabilizers used in that patent comprised several types of organic compounds containing, concurrently or individually, one or more nitrogen or phosphorus atom, or carboxyl group (COOH):

1. N,N,N$^1$,N$^1$-btetramethyl-o-phenylenediamine and 2,3$^1$-dipyridyl

2. HOOC-Y$_1$-COOH and

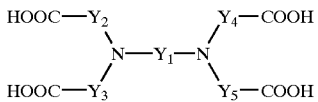

where: Y$_1$=(CX$_1$X$_2$)$_m$,m=2–10  Y$_2$,Y$_3$,Y$_4$,Y$_5$=(CX$_1$X$_2$)$_n$n= 2–10

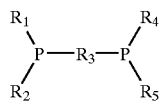

Where:
  R$_1$,R$_2$,R$_4$, and R$_5$ is an alkyl or an aralkyl having 1–20 carbon atoms;
  R$_1$,R$_2$,R$_{4,5}$ is an alkyl or an alkaryl having 6–20 carbon atoms
  R$_3$is a polymethylene group having 1–3 carbon atoms.

U.S. Pat. No. 5,001,259 described the use of inorganic iodides LiI as the stabilizer for the rhodium catalyst in the carbonylation of methanol to improve the precipitation of the rhodium catalyst under low water content, and obtained a reaction rate almost equal to that under high water content (14 wt. %). The same patent used also a quaternary ammonium salt, N-methyl-picolinium iodide, under low water content to increase the reaction rate of carbonylation. However, according to the result of the experiment, the N-methyl-picolinium iodide tended to form a hardly soluble complex with Rh that precipitated from the reaction solution. The nitrogen-containing compound, N-methylimidazole, mentioned in EP 1538341 tended also to form a hardly soluble complex with Rh that precipitated from the reaction solution of carbonylation of methanol.

In U.S. Pat. No. 5,442,107, six types of heterocyclic nitrogen compounds were employed as the catalyst stabilizer for the carbonylation of methanol under low water content:
  1. 2-ethyl-4-methylimidazole
  2. 4-methylimidazole
  3. 4-tert-butylpyridine
  4. 2-hydroxypyridine
  5. 3-hydroxypynidine
  6. 4-hydroxypyridine.

However, this patent did not disclose the effect of the additive used on the reaction rate under low water content. No alkyl pyridine was mentioned in that patent. Further, those catalyst stabilizers used in that patent were similar to those organic compounds mentioned in the prior art, i.e., picoline and N-methylimidazole, in that they tended to form a hardly soluble complex with Rh which precipitated from the reaction solution of carbonylation of methanol under low water content. These suggest that, if OH and tert-butyl were present on pyridine, there would be a significant effect of reducing the precipitation of the rhodium catalyst from the reaction solution of carbonylation of methanol under low water content. On the other hand, if no substituent was on pyridine or the substituent was a methyl group, such effect would be insignificant. Furthermore, the prior art has not mentioned or indicated that other pyridine derivatives having substituents other than OH or alkyl had the effect of reducing precipitation of the rhodium catalyst during the carbonylation of methanol under low water content.

Moreover, techniques that used complexes having a supported structure formed by coordinating an organic polymer with rhodium to prevent its precipitation in the reaction system under low water content and to increase further the concentration of the rhodium catalyst and hence the reaction rate were proposed. For example, Webber et al. described in Journal of Molecular Catalyst, 3 (1977/78) 1–9, that a polymer with two functional group was used in a carbonylation reaction. In the practical application of such polymer, however, there were still some problems such as lost of rhodium as well as their stability in the industrial application.

A rhodium complex formed by supporting rhodium with a 2,4-divinylpyridine was used in EP 277824 to perform a heterogeneous carbonylation reaction. In such a system, however, not only the activity of the catalyst was decreased significantly, but also the pyrolysis of the polymer itself or the reaction medium-mediated chemical decomposition of the polymer would resulted in the stripping of the rhodium off the polymer and the complicating of the purification system. Accordingly, such system has not been used in any industrial process.

As described in Journal of Catalyst, 40,255–267 (1975), a copolymer of a styrene having a diphenylphosphinyl group and a divinylbenzene was used as the support of rhodium in liquid and gas phase carbonylation reactions. ROC Patent Nos. 080618 and 094905 described the use of a series of phosphorus-containing liquid such as $PPh_3$ and $Ph_3PCH_2CH_2P(O)Ph_2$. However, in such a reaction system, dissociation of the polymer from the rhodium atom might cause the precipitation of the rhodium. Further, during the reaction, addition of excess of triphenylphosphine was necessary in order to keep so-claimed high catalytic activity.

Inorganic Chemistry, 20,641–644(1981) described reacting ion exchange resin such as Bio Rex 9 Dowex 1-X8 and the like or a copolymer of styrene and 4-vinylpyridine alkylated with methyl iodide with tetracarbonyl dichloro dirhodium or rhodium trichloride hydrate to form a heterogeneous catalyst. Although the author claimed that it could have a reaction effect comparable to that of a homogeneous catalyst, this was suggested by only an experimental result at low temperature of 120° C. and low pressure of 80–100 psi. In addition, when reacted in a liquid phase, a great amount of ion exchange resin must be maintained to proceed the reaction efficiently.

U.S. Pat. Nos. 5,281,395 and 5,466,874 used poly2-pyrrolidone crosslinked with divinylbenzene as a support for rhodium catalyst and carried out carbonylation of methanol under low water content to produce acetic acid or anhydride. As the experimental result indicated, although the rhodium complex catalust stabilized by such polymer could be funtioned at low water content, it was true only on the provision that a high cocentration of rhodium complex catalyst (e.g.,an alkyl iodides having an equalor even more carbon number) and an inorganic metal iodide must be present. It was undesirable in that excess metal iodides might lead to a corrosoin problem on the equipment used. Further, copolymers consist of 2-pyrrolidone had problems on the probability for formation of rhodium complex therewith and on the stability for long-time operation.

SUMMARY OF THE INVENTION

Accordingly, in view of overcoming the above-mentioned disadvantages of the prior art, one object of the invention is to provide a novel polymer-supported catalyst by supporting rhodium catalyst with a polymer.

Another object of the invention is to provide a process for preparing organic carboxylic acid or anhydride having n +1 carbon atoms by carbonylating with carbon monoxide on alcohols having n carbon atoms, ethers having 2n carbon atoms or esters formed from an alcohol with an acid, in the presence of the above-said polymer-supported catalyst system.

Still another object of the invention is to provide a process for preparing acetic acid by reacting methanol with carbon monoxide in the presence of the above-mentioned polymer-supported catalyst system.

DETAILED DESCRIPTION OF THE PREFERRED EMBODIMENTS

The polymer-supported catalyst according to the invention has a functional structure of formula

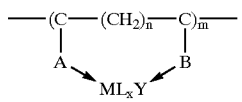

wherein:

A: is an unsaturated aliphatic or aromatic radical containing nitrogen, phosphorus or sulfur atom;

B: is A or an unsaturated aliphatic or aromatic alcohol, ether, aldehyde, ketone or carboxylic ester group containing oxygen, sulfur or phosphorus atom;

M: is rhodium, iridium or group VIII transitional metal;

L: is a carbonyl, triphenylphosphine or other ligand;

Y: is a halogen, tetraphenylboron, tetrafluoroboron, acetic acid, carbonate, bicarbonate or thiocyanate anionic radical;

x is 1 to 2;

n is 1–5;

m is 2–300.

In the process for preparing the above-said catalyst according to the invention, two type of monomers are used, namely, 2-vinyl pyridine and methyl acrylate, in an appropriate ratio in solution polymerization to form a copolymer. The copolymer thus obtained is used then to coordinate with rhodium compound such as rhodium chloride, rhodium iodide, rhodium acetate and the like to form polymer-supported rhodium catalyst. Before the coordination, those rhodium compounds must be selectively treated to reduce rhodium(III) into rhodium(I). This type of catalyst has advantages in that its stable structure can impart such catalyst system excellent thermal stability and chemical stability under the operation conditions of carbonylation reaction.

In another aspect of the invention, a process for preparing organic carboxylic acid or anhydride having n +1 carbon atoms by carbonylating with carbon monoxide on alcohols having n carbon atoms, ethers having 2n carbon atoms or esters formed from an alcohol with an acid, in the presence of the above-said polymer-supported catalyst system is provided. In the presence of such polymer-supported rhodium catalyst, when the reaction system is operated under a insufficient carbon monoxide partial pressure and an elevated temperature, due to the stability of its structure, the rhodium metal can be protected from precipitating in the reaction medium. Further, its catalytic activity can be maintained without adding excess hydroiodic acid such that the corrosion problem of equipment due to the addition of excess hydroiodic acid can be reduced greatly and hence save a lot of equipment investment.

In addition, in traditional "high water content" process for preparing acetic acid from methanol and carbon monoxide, water content of up to 14~15 wt % must be present in the reaction medium in order to increase the solubility of rhodium catalyst and enhance its catalytic activity. On the contrary, in the catalyst system according to the invention, the rhodium catalyst is in polymer-supported form, water content can no longer have a significant effect on the precipitation of the rhodium catalyst. Further, the high catalytic activity of the catalyst system according to the invention can overcome successfully the decrease of reaction rate under low water content associated with the traditional process and hence retain a relatively excellent reaction performance. As the water content is lowered, production capacity of a reactor having a same size can be increased. Further, the corrosion problem caused by moisture reaction to the reaction system due to a large amount of water in the reaction system can be avoided. Moreover, the elimination of the load on the separation equipment can have a somewhat benefit for the investment efficacy. Particularly, as the water content is lower than a given ratio, esters in the reaction system can be reduced as the reaction proceeds and thereby acid or anhydride can be formed such that the utility and yield of the process can be extended relatively.

In the practice of the process according to the invention, alcohol, ester of the alcohol with the carboxylic acid as the desired product, or the carboxylic acid itself, together with carbon monoxide, polymer-supported rhodium catalyst, organic iodine derivative, a selected ratio of hydroiodic acid, inorganic halide, stabilizer for catalyst and water are charged into a carbonylation reactor. Among them, the polymer-supported rhodium catalyst, organic iodine derivative, hydroiodic acid, inorganic halide, metal acetate, and the stabilizer for catalyst will not be consumed during the reaction and will return continuously to the reactor through a flashing tank or a separation and purification apparatus. In correspondence with continuous addition of various raw materials into the carbonylation reactor, the effluent product of the system according to the invention contains the carboxylic acid product and the corresponding anhydride, the rhodium catalyst and the iodine derivative. Further, in the reaction system according to the invention, when a steady sate of a homogeneous or heterogeneous phase is maintained in the carbonylation reactor, the reaction medium can have a given amount of polymer-supported rhodium catalyst, organic iodine promoter, alcohol, ester of the carboxylic acid and the carboxylic acid itself, as well as a selected ratio of hydroiodic acid, inorganic halide and water. The carbonylation reactor contains actually, however, only small amount of free alcohol, since esterification reaction of alcohol with acid proceeds quiet rapidly.

For the process according to the invention, the composition of various reaction components in the homogeneous or heterogeneous reaction medium at a steady state is preferably within the range listed in Table 1:

TABLE 1

The suitable and optimal compositions of various reaction components.

| Reaction components | Suitable range | Preferred range |
|---|---|---|
| Ester of alcohol and acid | 0.1 ~ 30 wt % | 0.1 ~ 5 wt % |
| Organic iodine promoter | 5 ~ 40 wt % | 10 ~ 30 wt % |
| Polymer-supported rhodium catalyst(weight ratio of rhodium catalyst/polymer) | 200 ~ 5000 ppm (1 ~ 40 wt %) | 500 ~ 2000 ppm (5 ~ 20 wt %) |

TABLE 1-continued

The suitable and optimal compositions of various reaction components.

| Reaction components | Suitable range | Preferred range |
|---|---|---|
| Water content | 0 ~ 20 wt % | 1 ~ 10 wt % |
| Hydroiodic acid | 0 ~ 30 wt % | 3 ~ 20 wt % |
| Inorganic halide or acetate | 0 ~ 30 wt % | 3 ~ 20 wt % |

In another aspect of the invention, a process for preparing acetic acid by carbonylation of methanol in the presence of the instant polymer-supported rhodium catalyst, the preferable composition may be as follows:

methyl acetate, 0.1~5 wt %;

methyl iodide, 10~30 wt %;

polymer-supported rhodium catalyst, 500~2000 ppm;

water, 1~10 wt %;

hydroiodic acid, 3~20 wt %;

inorganic halide or acetate, 3~20 wt %; and acetic acid of the remainder.

In the process according to the invention, temperature of the carbonylation reactor is suitably kept at 100~250° C., and the higher the temperature, the reaction rate is faster. Preferred temperature is in the range of 160~220° C. The pressure of carbon monoxide is maintained at 10~200 atmospheric pressure, preferably in the range of 20~60 atmospheric pressure.

EXAMPLES

The invention will be illustrated in more detailed by the following Examples that do not intend to limit the scope of the invention in any way.

Apparatus used in the process of the instant invention comprise mainly a one-liter reactor made of corrosion-proof material, and a carbon monoxide storage tank. The reactor is provided with a speed variable motor for controlling rotation speed in a suitable range to maintain a good gas-liquid mixing effect. The reactor is provided further an external and internal cooling coil and an electric heater to control and maintain a stable reaction temperature. A pressure control valve is provided between the reactor and the carbon monoxide storage tank for controlling and keeping the pressure in the main reactor.

In these Examples, the pressure of the reactor is kept at 400 psi. For operation of the reaction, the reactant such as methanol was added into a mixture consisting of the catalyst, the organic iodine promoter, or optionally added water, hydroiodic acid, and inorganic halide, and reacted at a constant temperature and pressure. For comparison of reaction rates, all rate data were expressed in Space Time Yield (STY) established by B. L. Smith et al. Reaction productivity was calculated as number of mole of acetic acid produced per unit volume per unit time. The space time yield could be obtained from the consumption rate of carbon monoxide contained in the storage tank, the volume of the carbon monoxide storage tank and the volume of the reaction solution. Therefore, in the course of the reaction, the change of the pressure of carbon monoxide in the storage tank was monitored continuously to obtain the consumption rate of the carbon monoxide.

During the operation, if required by the requirement, 10 ml of reaction solution was taken from the sampling port of the reactor for performing iodine titration, gas chromatography and atomic absorption spectrometry. The catalytic rate in the course of the reaction could be estimated from these analytic data and the volume of carbon monoxide consumed at that time. At the end of the carbonylation reaction, the temperature of the reactor was lowered to room temperature, all of the reactants were discharged and its total reaction volume was measured. The space time yield of the total reaction was calculated from the total consumption of carbon monoxide and analytical data.

Example 1 preparations of polymer and polymer-supported rhodium catalyst 99 g vinylpyridine, 327 g methyl acrylate, 6.4 g azobis-(isobutyronitrile) and 1000 g benzene were solution polymerized at 65° C. for 5 hours. The reaction solution was poured in ether to yield a gel-like precipitate. The precipitate was filtered out and dried in an oven. About 500 g of the desired polymer was obtained as a pale yellow solid.

The resulting polymer was dissolved in methanol or acetic acid and used for preparing polymer-supported rhodium catalyst through either of the two approaches below. One approach comprised mixing, in a ratio of 5 wt %, a solution of tetracarbonyl dichloro dirhodium in methanol with the polymer above. A precipitating agent immiscible with the solvent, such as sodium tetraphenylboron, sodium tetrafluoroboron, metal acetate, metal carbonate and the like was used to remove chlorine or iodine from the precipitate. After drying, a polymer-supported rhodium catalyst according to the invention was obtained. In the second approach, a solution of dicarbonyl diiodo rhodium in acetic acid or an aqueous solution of rhodium acetate was added respectively in the reaction solution together with the polymer obtained above and reacted directly to give a result same as the first approach.

Example 2

For comparison with the instant polymer-supported rhodium catalyst, in this example, carbonylation reactions were performed with traditional acetic acid process. Composition of reactants in the reactor comprised of water, 10 wt %; methyl iodide, 15 wt. %; and the concentration of rhodium, 640 ppm. The reaction was carried out at a temperature of 185 ° C. and a pressure of 29 kg/cm$^2$. The resulting STY was 4.58.

Example 3

In this Example 3, operation conditions and the composition of reactants were same as in Example 2, except that 3 wt % of hydroiodic acid was added. The resulting STY was 5.83.

Example 4

In this Example 4, the composition of reactants was same as in Example 2, except that polymer prepared as in Example 1 was added (weight ratio of rhodium to the polymer was 5 wt %). The resulting STY was 5.63.

Example 5

In this Example 5, 3 wt % hydroiodic acid was added, as in Example 3. After reacting under a condition same as in Example 2, a STY of 6.8~6.82 was obtained.

It is found from Table 2 that, under the same situation of absence of hydroiodic acid, the reaction rate obtained in the presence of the polymer-supported rhodium catalyst was higher than that obtained in the traditional process. After addition of hydroiodic acid, the same effect of increasing the reaction rate still existed.

Example 6/7

In Example 6, a solution of suitable amount of polymer-supported rhodium catalyst containing 5 wt % rhodium prepared from tetracarbonyl dichloro dirhodium was added to a solution of 10 wt % water and a solution of 15 wt % methyl iodide, respectively (in Example 7, 3 wt % of hydroiodic acid was added in addition). A carbonylation reaction was carried out at a rhodium concentration of 640 ppm, a temperature of 185° C. and a pressure of 29 kg/cm$^2$. Resulting STY was 5.75 and 7.59, respectively.

Example 8/9

In Example 8, a mixture of the polymer prepared as in Example 1 and a solution of rhodium in acetic acid was added to a solution of 10 wt % water and a solution of 15 wt % methyl iodide, respectively (in Example 9, 3 wt % hydroiodic acid was added in addition). A carbonylation reaction was carried out at a rhodium concentration of 640 ppm, a temperature of 185° C., and a pressure of 29kg/cm$^2$. STY resulted were 6.62 and 7.07, respectively in Example 7~8, whether hydroiodic acid was added or not, reaction rates obtained were higher than that in Example 2.

It could be seen from Example 2~9 that, whether hydroiodic acid was added or not, the performance of polymer-supported catalyst prepared from rhodium acetate was better than that of the catalyst prepared from tetracarbonyl dichloro dirhodium and further better than that prepared from dicarbonyl diiodo dirhodium.

Example 10~12

In order to demonstrate the advantage of the polymer-supported catalyst according to the invention, to reactors containing 15 wt % methyl iodide and 3 wt % hydroiodic acid, respectively, suitable amount of dicarbonyl diiodo rhodium solution was added and water contents were adjusted to 10 wt %(Example 10) 7.24wt %(Example 11) and 4.53wt % (Example 12), respectively. Carbonylation reactions were carried out at a rhodium concentration of 590 ppm, a temperature of 185° C., and a pressure of 29 kg/cm$^2$. STY values obtained were 5.41, 5.53 and 5.63, respectively.

In comparison with Example 2, under a low water content, the polymer-supported catalyst could indeed retain a reaction rate comparable to or even better than that obtained in a traditional process.

Example 13~15

Where appropriate, for using in a traditional process comprising of adding hydroiodic acid, addition of polymer in a proper ratio relative to rhodium catalyst under low water content, an excellent result similar to those of Example 10~12 could be obtained. In Example 13~15, the operation procedure was same as in Example 10~12, except that 3 wt % hydroiodic acid was added further and water contents were adjusted to 10 wt % (Example 13) 5wt %(Example 14) and 0.6wt %(Example15), respectively. Carbonylation reactions were carried out at a rhodium concentration of 590 ppm, a temperature of 185° C., and a pressure of 29 kg/cm$^2$. STY values obtained were 6.58, 7.43, and 6.60, respectively.

TABLE 2

Comparison of reaction rates of Example2 ~ 15

| polymer | Water content (wt %) | Methyl iodide (wt %) | Hydroiodic acid (wt %) | Rh Conc'n (ppm) | STY |
|---|---|---|---|---|---|
| Example2 | 0 | 10 | 15 | 0 | 640 | 4.58 |
| Example3 | 0 | 10 | 15 | 3 | 640 | 5.83 |
| Example4 | 1.28% | 10 | 15 | 0 | 640 | 5.63 |
| Example5 | 1.28% | 10 | 15 | 3 | 640 | 6.82 |
| Example6 | 1.28% | 10 | 15 | 0 | 640[a] | 6.62 |
| Example7 | 1.28% | 10 | 15 | 3 | 640[a] | 7.07 |
| Example8 | 1.28% | 10 | 15 | 3 | 640[b] | 6.62 |
| Example9 | 1.28% | 10 | 15 | 3 | 640[b] | 7.07 |
| Example10 | 1.18% | 10 | 15 | 0 | 590 | 5.41 |
| Example11 | 1.18% | 7.24 | 15 | 0 | 590 | 5.53 |
| Example12 | 1.18% | 4.53 | 15 | 0 | 590 | 5.63 |
| Example13 | 1.18% | 10 | 15 | 3 | 590 | 6.58 |
| Example14 | 1.18% | 5 | 15 | 3 | 590 | 7.43 |
| Example15 | 1.18% | 0.6 | 15 | 3 | 590 | 6.60 |

[a]: polymer-supported catalyst prepared from tetracarbonyl dichloro dirhodium.
[b]: adding after mixing a rhodium acetate solution with the polymer, while in other cases, adding after mixing a dicarbonyl diiodo rhodium solution with the polymer.

The invention has following advantages:

(1) low corrosive reaction conditions: the polymer-supported catalyst is active in the absence of hydroiodic acid or is active after lowering properly contents of hydroiodic acid and water. Therefore, it can reduce strong acidic hydrolysis and moisture reaction due to the presence of excess hydroiodic acid and water such that the corrosion problem of the system can be reduced and the investment cost can be greatly lowered while still achieve a relatively excellent catalytic activity for the carbonylation reaction.

(2) Mild reaction condition: at a reaction temperature of 160° C., a reaction rate comparable to that in traditional reaction system can be obtained such that energy consumption and equipment requirement can be accordingly reduced, which is favor for the promotion of production benefit.

(3) High catalytic activity and high stability: the polymer-supported catalyst of the instant invention can increase the carbonylation reaction rate during production of carboxylic acid and enhance the stability of rhodium complex.

(4) High temperature-resistant reaction condition: polymer used in the instant invention has a heat decomposition temperature of as high as 220° C., which is much better than any polymer disclosed in prior art patents and any ion exchange resin. After selectively partially crosslinked with divinylbenzene, its heat decomposition temperature can be increase to higher than 250° C., which not only facilitates increasing reaction temperature and catalytic activity thereof, but also makes them being suitable for various existing carbonylation process without modification of any equipment.

(5) Operable under low water content: since the rhodium catalyst of the instant invention is in a form of being supported by a polymer, water content can not affect significantly on the precipitation of the rhodium catalyst. Further, the high catalytic activity of the instant catalyst has overcome the lowering of reaction rate occurred under low water content such that it can maintain a relatively excellent reaction performance. As the water content is decreased, reactor of same size can increase gradually its production capacity. Accordingly, in addition to avoid the corrosion problem on the reaction system caused by moisture attack and to reduce the burden on process separation equipment due to the presence of a large amount of water in the reaction system, it can afford somewhat benefit to investment efficacy.

(6) Selectively production of organic carboxylic acid or anhydride: by using the instant polymer-supported catalyst, when the water content is lower than a given weight %, esters contained in the system will be reduced as the reaction proceeds and thereby promotes the production of acid or anhydride, which can correspondingly extend the utility and yield of the process.

Many changes and modifications in the above-described embodiment of the invention can, of course, be carried out without departing from the scope thereof. Accordingly, to promote the progress in science and the useful art, the invention is disclosed and is intended to be limited only by the scope of the appended claims.

What is claimed is:

1. A polymer-supported carbonylation catalyst useful in a process for preparing organic carboxylic acid or anhydride having n −1 carbon atoms by carbonylating with carbon monoxide-on;alcohols having n carbon atoms, either having 2n carbon atoms or ester of said alcohol with an acid, wherein the polymer in said polymer-supported catalyst can be crosslinked to have a functional structure of:

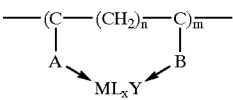

where:

A: is an unsaturated C1–5 aliphatic radical containing nitrogen or an aromatic radical containing nitrogen;

B: is A or an unsaturated C1–5 aliphatic or aromatic alcohol, ether, aldehyde, ketone or carboxylic ester group containing oxygen;

M: is rhodium or iridium;

L: is a carbonyl, triphenylphosphine or other ligand;

Y: is a halogen, tetraphenylboron, tetrafluoroboron, acetic acid, carbonate, bicarbonate or thiocyanate anionic radical;

x is 1 to 2;

n is 1–5;

m is 2–300.

2. A polymer-supported carbonylation catalyst as in claim 1, wherein functional group A is a hydrocarbyl, cyclohydrocarbyl or heterocyclohydrocarbyl group wherein said hydrocarbyl, cyclohydrocarbyl and heterocyclohydrocarbyl contains nitrogen.

3. A polymer-supported carbonylation catalyst as in claim 1, wherein functional group B is acrylonitrile, acrolein, butyroketene, methyl acrylate or ethyl acrylate.

4. A polymer-supported carbonylation catalyst as in claim 1, wherein $ML_xY$ is a dicarbonyl rhodium or a monocarbonyl monohalo rhodium.

5. A polymer-supported carbonylation catalyst as in claim 1, wherein the polymer in said polymer-supported carbonylation catalyst is prepared by copolymerizing (A) with itself or by copolymerizing (A) with B at a copolymerization ratio of A to B in the range of 10:1 to 1:20; wherein A is an unsaturated C1–5 aliphatic compound containing nitrogen or an aromatic compound containing nitrogen and (B) is an unsaturated aliphatic or aromatic alcohol, ether, aldehyde, ketone or carboxylic ester containing oxygen.

6. A polymer-supported carbonylation catalyst as in claim 1, wherein said crosslinked polymer is prepared by adding crosslinking agent during the polymerization according to claim 5.

7. A polymer-supported carbonylation catalyst as in claim 6, wherein said crosslinking agent is divinylbenzene.

8. A process for preparing organic carboxylic acid or anhydride having n+1 carbon atoms by carbonylating with carbon monoxide on alcohols having n carbon atoms, ether having 2n carbon atoms or ester of said alcohol with an acid, said process comprising carrying out a carbonylation reaction by using, at a suitable temperature, in a reaction medium:

(1) a polymer supported carbonylation catalyst characterized in a structural unit of

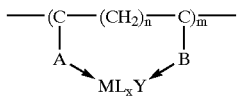

where:
A: is an unsaturated C1–5 aliphatic containing a nitrogen atom or an aromatic radical containing nitrogen;
B: is A or an unsaturated C1–5 aliphatic or aromatic alcohol, ether, aldehyde, ketone or carboxylic ester group containing oxygen;
M: is rhodium or iridium;
L: is a carbonyl, triphenylphosphine or other ligand;
Y: is a halogen, tetraphenylboron, tetrafluoroboron, acetic acid, carbonate, bicarbonate or thiocyanate anionic radical;
x is 1 to 2;
n is 1–5;
m is 2–300; and (2) an organic iodine promoter.

9. A process as in claim 8, wherein said reaction medium comprises further a selected ratio of hydroiodic acid.

10. A process as in claim 8 or 9, wherein said reaction medium comprises further a selected ratio of inorganic halides or acetates.

11. A process as in claim 10, wherein said reaction medium comprises further a selected ratio of water.

12. A process as in claim 8 or 9, wherein said reaction medium comprises further a selected ratio of water.

13. A process as in claim 8, wherein said carbonylation reaction is used for preparing acetic acid from carbonylating methanol with carbon monoxide.

14. A process as in claim 8, wherein said polymer-supported carbonylation catalyst comprises a weight ratio of rhodium to said polymer in the range of 1~40 wt %.

15. A process as in claim 8, wherein said polymer-supported carbonylation catalyst comprises preferably a weight ratio of rhodium to said polymer in the range of 5~20 wt %.

16. A process as in claim 8, wherein said polymer-supported carbonylation catalyst is a homogeneous catalyst in said reaction medium.

17. A process as in claim 8, wherein said polymer-supported carbonylation catalyst is a non-homogeneous catalyst in said reaction medium.

18. A process as in claim 8, wherein said polymer-supported carbonylation catalyst comprises a rhodium concentration in said reaction medium in a range of 200~5000 ppm.

19. A process as in claim 8, wherein said polymer-supported carbonylation catalyst is added in a manner by adding said polymer-supported carbonylation catalyst directly in said reaction medium.

20. A process as in claim 8, wherein said polymer-supported carbonylation catalyst is added in a manner by adding separately said polymer, catalytic metal compounds and assisting additives in said reaction medium.

21. A process as in claim 20, wherein said metal compound is a compound of rhodium or iridium.

22. A process as in claim 21, wherein said catalytic metal compound is tetracarbonyl dichloro dirhodium, rhodium acetate or rhodium hydroxide.

23. A process as in claim 20, wherein said assisting additives is sodium tetraphenylboron, sodium tetrafluoroboron, metal acetate, metal carbonate, metal bicarbonate, metal thiocyanate, iodonium acetate, or metal halide.

24. A process as in claim 8, wherein said organic iodine promotor is present in said reaction medium in an amount of 5~40 wt %.

25. A process as in claim 8, wherein said organic iodine promotor is preferably present in said reaction medium in an amount of 10~30 wt %.

26. A process as in claim 25, wherein said organic iodine promotor is alkyl iodide.

27. A process as in claim 8, wherein said selected ratio of inorganic halides or acetates is present in said reaction medium in an amount of 0~30 wt %.

28. A process as in claim 8, wherein said selected ratio of inorganic halides or acetates is present preferably in said reaction medium in an amount of 3~20 wt %.

29. A process as in claim 28, wherein said selected ratio of inorganic halides or acetates is a halide or acetate of alkaline metal, alkaline earth metal or transitional metal.

30. A process as in claim 8, wherein said selected ratio of hydroiodic acid is present in said reaction medium in an amount of 0~30 wt %.

31. A process as in claim 8, wherein said selected ratio of hydroiodic acid is present preferably in said reaction medium in an amount of 3~20 wt %.

32. A process as in claim 8, wherein said water is present in said reaction medium in an amount of 0.5~20 wt %.

33. A process as in claim 8, wherein said water is present preferably in said reaction medium in an amount of 5~10 wt %.

34. A process as in claim 8, wherein said reaction temperature is 100~250° C.

35. A process as in claim 8, wherein said reaction temperature is preferably 160~220° C.

36. The process of claim 18 wherein said rhodium concentration in said reaction medium is in the range of 500–2000 ppm.

* * * * *